United States Patent [19]

Merck, Jr. et al.

[11] Patent Number: 6,142,010
[45] Date of Patent: *Nov. 7, 2000

[54] PENETRATION HARDNESS TESTER

[75] Inventors: John J. Merck, Jr., Medfield; Jon Wyman, Somerville; Richard Conti, Foxboro, all of Mass.

[73] Assignee: Instron Corporation, Canton, Mass.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/821,461

[22] Filed: Mar. 21, 1997

Related U.S. Application Data

[63] Continuation of application No. 08/591,292, Jan. 25, 1996, Pat. No. 5,616,857.

[51] Int. Cl.[7] .................................................. G01N 3/42
[52] U.S. Cl. ................................................................ 73/81
[58] Field of Search .............................. 73/12.09, 12.12, 73/81–83, 78

[56] References Cited

U.S. PATENT DOCUMENTS

| | | | |
|---|---|---|---|
| 4,094,188 | 6/1978 | Bellouin et al. | 73/81 |
| 4,111,039 | 9/1978 | Yamawaki et al. | 73/81 |
| 4,671,104 | 6/1987 | Fischer | 73/81 |
| 4,820,051 | 4/1989 | Yanagisawa et al. | 73/81 |
| 5,067,346 | 11/1991 | Field | 73/81 |

*Primary Examiner*—Robert Raevis
*Attorney, Agent, or Firm*—Levisohn, Lerner, Berger & Langsam

[57] ABSTRACT

A hardness tester is disclosed which conducts its hardness test through a penetrator impinging upon the surface of a test specimen. Enhanced accuracy and repeatability is achieved through the use of a closed loop system and directly mounting a load cell to the indentor, connecting a linear displacement transducer directly to the load cell and eliminating an elevating screw in initially positioning and applying load to the specimen to be tested.

20 Claims, 1 Drawing Sheet

# PENETRATION HARDNESS TESTER

This application is a continuation of application Ser. No. 08/591,292 filed Jan. 25, 1996 which application is now U.S. Pat. No. 5,616,857.

BACKGROUND OF THE INVENTION

The present invention is directed to apparatus to determine the hardness or other properties of materials and includes a penetration hardness tester.

Penetration hardness testers are well-known in the art, and generally include a diamond or ball tipped penetrator and means to apply minor or major loads of predetermined magnitudes through the penetrator to a test specimen in successive load cycles. The hardness of the surface being tested produces results such as a Rockwell number or Brinell number. The hardness is related to the depth of penetration of the penetrator into the surface when a selectable value of compressive force is applied to the penetrator.

In prior art Rockwell type hardness testers, the force that is exerted on the penetrator is produced by gravity acting on weights, and this in turn is transferred by mechanical means to the penetrator. The depth of penetration is generally directly measured from the tool and generally displayed on a dial indicator, digital display or other display apparatus. Prior art apparatus requires gravity acting on weights, and the measurement of the tool movement through mechanical assemblies is subject to impreciseness as the tester is repeatedly utilized subjecting the apparatus to wear through repeated mechanical movement.

The use of deadweight testers and their mechanical impreciseness over time has led to the use of a load cell as a means to apply load to the test specimen. An example of a system employing a load cell is found in U.S. Pat. No. 4,535,623 entitled Material Hardness Testing Apparatus by Paul Gilberto. That patent is assigned to a predecessor of the assignee of the present application. In the '623 patent, a load cell 26 is located adjacent the penetrator 27, and deadweights are avoided in conducting the hardness tests. A mechanical threaded advancing means is employed to apply the load to the test specimen, and the load on the load cell is related to the force on the test specimen. The mechanical action in the '623 patent for applying force by the tester, by its very nature, will, over time cause impreciseness because of the relative movement of the threaded screw and its driven elements. Such inaccuracies can become significant in the measurement process as the underlying measurements are used as a basis for many determinations thereafter.

The use of feedback control closed loop systems can lessen the impreciseness which is attendant to materials hardness tests. U.S. Pat. No 4,435,976 describes the use of a load cell to determine the forces applied during Brinell tests and employs a feedback loop to automatically compensate factors which affect the accuracy of the measurements, such factors being temperature and friction. The apparatus in the '976 patent utilizes a mechanical bearing connected between the indenter and the load cell, which mechanical bearing, itself, can cause inaccuracies in the measurement process because of its repeated mechanical movement and the wearing of the bearing.

The indentor will penetrate to some depth or displacement in the test specimen. A measurement is made of the displacement, and in prior art penetration hardness testers, there are moving mechanical parts which move relative to each other located between the actual displacement and measured displacement. Such relative mechanical movement can contribute to sources of friction or lost (nonrecoverable) displacement between the point of displacement measurement and the test specimens so as to impair the repeated accuracy of the hardness test.

All known bottom-referencing type hardness testing machines, both using load cell and deadweight style, employ an elevating screw to accommodate different specimen sizes. The mechanical forces employed in the elevating screw also can contribute to degradation of displacement measurement accuracy because of the possibility of additional deflection loss which can contribute to the inaccuracy of the displacement measurement.

An object of this invention is to provide an improved hardness tester which eliminates the inaccuracies of prior hardness testing apparatus.

Another object of the present invention is to provide such an improved apparatus which is easy to operate, substantially unchanging over time and location and produces reliable and accurate results.

Yet another object of this invention is to provide such an apparatus which advantageously employs current technology to provide improved results and may be readily adapted to provide additional test data.

Other objects, advantages, and features of this invention will become apparent from the following description.

Detailed Description

Figure 1:
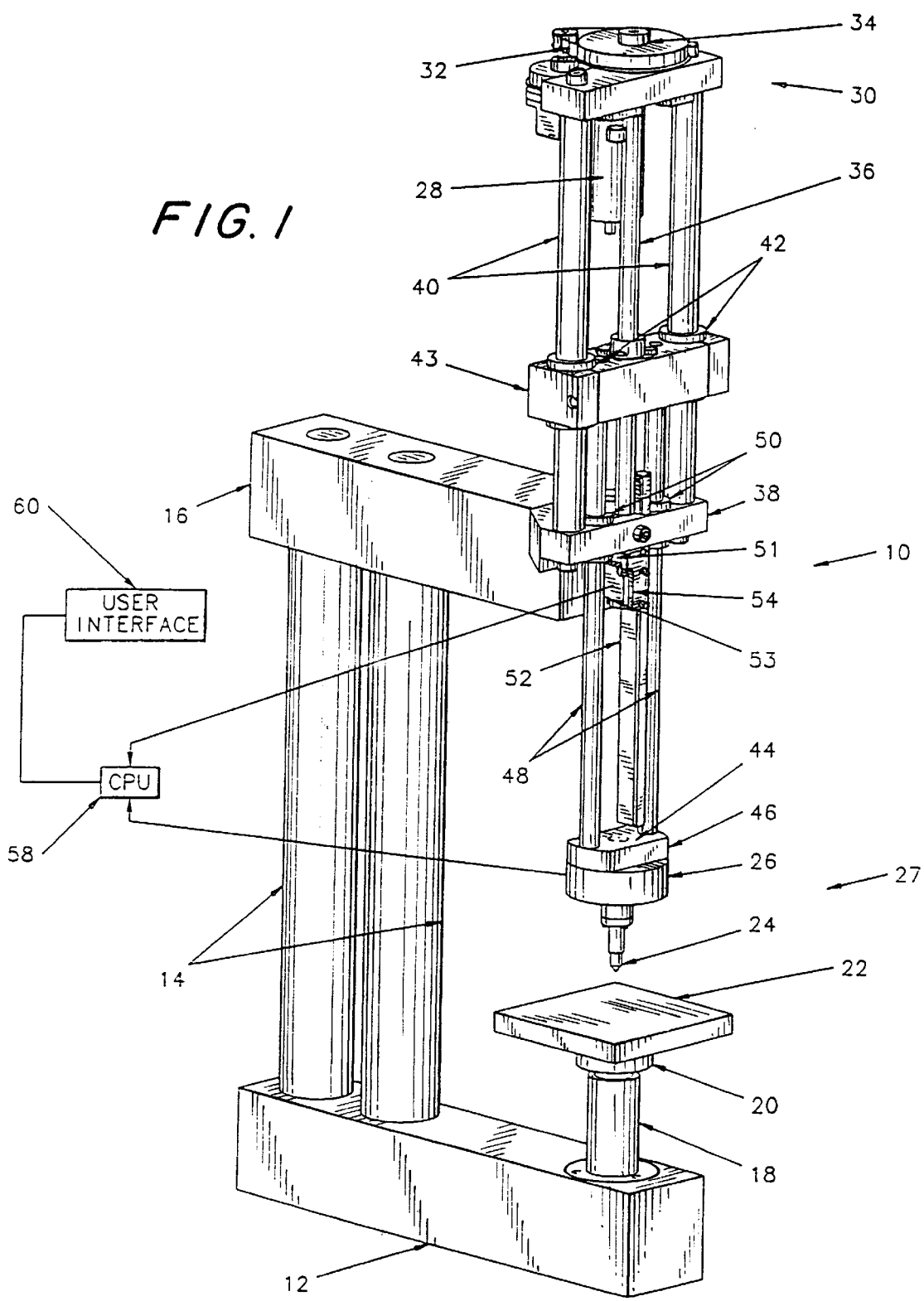
FIG. 1 is a perspective view of the testing apparatus of the present invention.

The testing apparatus 10 of the present invention comprises a substantially rectangular base 12 upon which the tester is built and rests. A pair of cylindrical support columns 14 are connected between the base 12 and a rectangular support platform 16. Support platform 16 is considered a part of the frame formed of base 12 and support columns 14.

In general terms, the hardness tester comprises a support platform 18 located on base 12 on which an anvil 20 is located with the material 22 to be tested being placed on the top surface of anvil 20. An indentor 24 is located directly above anvil 20, and the indentor 24 is directly connected to a load cell 26. Th e load cell and indentor are movable with respect to platform 16.

In prior art hardness testing machines, an elevating screw is generally provided to raise the specimen to be tested to properly be located with respect to the indentor. The mechanical operation of the elevating screw includes frictional losses, and over time, inaccuracies in measurements can occur because of potential lost deflection relating to mechanical losses in the elevating screw mechanism. In accordance with a principal of the present invention, the hardness tester of this invention includes multiple size positions for the tests without using an elevating screw. Since the initial position of the indentor is easily controlled. It is not necessary to move the test specimen upwardly with an elevating screw, but accommodation for different sizes may be made by use of different sized platforms to provide different discrete vertical positions. Additionally, the tester includes the ability to move the actuator under non-load conditions to an initial starting position.

Movement of the indentor 24 is accomplished by controlling a motor 28 located at the top 30 of the apparatus 10. The motor drives a belt 32 which rotates a hub 34 which rotates a threaded ball screw 36. A pair of guide rods 40 straddle ball screw 36 and round bearings or slide members 42 permit movement of an intermediate platform 43. Lower platform 38 is fixed to frame 16, and intermediate platform 43 is moved by ball screw 36. Platform 43 is connected to the top 44 of load cell connector 46 by a pair of inner columns 48 with the pair of inner columns moving with platform 43 and slidably moving through collars 50 located in fixed lower platform 38.

When motor 28 rotates, ball screw 36 rotates which moves intermediate platform 43 which then moves the indentor because the movement of intermediate platform 43 is carried by columns 48 to the indentor 24.

Lower platform 38 is fixed to frame 16 and a reading head 53 is also fixed thereto. A glass scale 52 is attached to the columns 48 adjacent glass scale 52 so that as the columns 48 move, the amount of its vertical displacement is sensed. The glass scale 52 and reading head may be adjusted with respect to each other by adjustment member 54.

The movement of glass scale 52 with respect to head 53 provides an electrical signal which is connected to a central processing unit 58, which also receives as an input an output of load cell 26. A user interface 60 is also connected to the central processing unit 58 to provide display readings, identify parameters of operations, enter control information and display test results during the testing operations.

The displacement transducer formed of glass scale 52 and reading head 53 preferably, is a Heidenhain LIF displacement transducer. It is positioned such that the displacement measurement occurs directly above the load cell and below any actuator bearing or drive components. Specifically, glass scale 52 is attached to the inner columns 48 which connects to the load cell. The reading head 53 is attached to the actuator mounting plate 51, which in turn, is fastened to lower platform 38 and therefore, to the frame of platform 16 of the device. By locating the displacement transducer as described above, there are no sources of friction or lost non-recoverable displacement between the point of displacement measurement and the test specimen. (There is always load cell hysteresis and creep which may cause negligible displacement errors). As such, the measured displacement is due "solely" to the specimen deformation and nothing else. A benefit resulting from this arrangement is that the specimen deformation is measured with maximum possible accuracy. In the prior art, the displacement transducer is located "above" the load application system which requires intervening mechanical frictional action, thereby reducing the accuracy of prior art systems.

In accordance with an aspect of the invention, a closed loop system is provided which is responsive to loads applied to the indentor 24 and test specimen 22 by setting a desired load in the CPU 58 and sensing the load applied at the load cell 26.

Another aspect of the present invention is the ability to accurately control the rate of application of the load, and the control system of this invention provides means to determine the rate of application of the load system.

The control loop of the present invention is a proportional integral derivative gain control loop with real time stiffness compensation. This type system enhances sensing an error signal in the closed loop to intensify the sensitivity of the apparatus. The use of the reading head and glass scale provides improved operation because of the direct observation of movement. Fiber optic and/or laser devices may also be effectively used to sense the position or location of the actuator 27.

In accordance with an aspect of the present invention, by employing a closed loop system with the electrical motor 28, the pretest positioning may be achieved much more quickly and essentially unlimited test specimen weights can be utilized. By employing the central processing unit 58, improved data gathering will be realized including scale changing and other aspects of the testing procedures. Further, in addition to the rate of application of the load, the amount of penetration as well as other parameters in the measuring process may also be sensed and utilized to further define the mechanical properties of the materials being tested. The tester includes the ability to produce related pairs of information about the displacement and related load. The tester, therefore, can identify and cancel out any displacements not specifically the result of specimen deformation, as well as locate the surface of the specimen from the data pairs. As a result, the tester can determine the actual depth of indenter penetration into the specimen for any given load.

In the present invention, there is less maintenance because there is less mechanical movement between connected parts, and the elimination of such mechanical movement eliminates inaccuracies due to friction of dirt buildup and repeated mechanical use. This is especially true with the load cell being directly coupled to the indentor without intervening moving parts. Thus, all moving mechanical parts are within the closed loop system and since the closed loop load control system continually compensates for friction of dirt buildup and mechanical wear, improved performance is achieved. This provides more reliable, repeatable testing over time and allows better comparison of data obtained from testers in different locations.

Additionally, indentor protection is provided because the actuator 27 movement can be stopped if an increase in the load is not accompanied by a proper change in depth measurement, with the depth measurement being sensed by the displacement transducer. Further, load dwell times and loading rates can be controlled more accurately and altered for specific applications and load and depth data are available for further material properties analysis.

As a feature of this invention, "smart" indentors may be employed with this system in which calibration factors for different measurements can automatically be loaded into the system to automatically compensate for changes or differences which occur in the different indentors.

This invention has been described with reference to a preferred embodiment and other embodiments are considered within the scope of this invention as defined by the appended claims.

What is claimed:

1. A hardness tester for performing materials hardness testing on a test specimen, said hardness tester comprising:

indentor means for creates a deformation in the specimen;

motor means for generating motive power;

actuator means for transmitting said motive power into vertical movement;

load cell means for generating a load directly coupled to said indentor means;

linear displacement transducer means for sensing the amount of vertical movement of said actuator means and said indentor means;

closed loop control means for applying load to the test specimen and for controlling indentor means movement; and user interface means for displaying test parameters and test results and for providing electrical signals to direct a test operation run by said hardness tester, wherein said linear displacement transducer means and said closed loop control means in combination control non-load vertical movement of said indentor means resulting from an electrical feedback signal from said linear displacement transducer means which is indicative of the amount of vertical movement of said indentor means, and wherein said load cell and said closed loop control system means in combination control movement of said indentor means resulting from an electrical feedback signal from said load cell means which is also indicative of the amount of load applied to said load cell means and said indentor means.

2. A hardness tester for performing materials hardness testing according to claim 1, wherein said closed loop control means comprises a load closed loop system.

3. A hardness tester for performing materials hardness testing according to claim 2, wherein said load closed loop system comprises a proportional integral derivative gain control system with real time stiffness compensation.

4. A hardness tester for performing materials hardness testing according to claim 3, wherein said linear displacement transducer means comprises an optical grating scale and means for sensing the amount of movement by said actuator means with respect to said scale.

5. A hardness tester for performing materials hardness testing as claimed in claim 2, wherein said linear displacement transducer means is located directly above said load cell means for directly measuring displacement in the test specimen.

6. A hardness tester for performing materials hardness testing as claimed in claim 2, further comprising frame means for supporting said tester, wherein said linear displacement transducer means includes a glass scale attached to said actuator means, and a reading head attached to said frame means, wherein said glass scale moves with respect to said reading head and enables direct measurement of displacement of said actuator means.

7. A hardness tester for performing materials hardness testing as claimed in claim 2 further comprising a specimen support platform located on a base of said tester, said specimen support platform being selectable from a plurality of specimen support platforms of differing sizes.

8. A hardness tester for performing materials hardness testing as claimed in claim 2 wherein said tester comprises means for producing information about the test load and related test displacement substantially simultaneously.

9. A hardness tester for performing materials hardness testing as claimed in claim 2 wherein said tester comprises means for measuring the depth of specimen indentation from the surface of the test specimen.

10. A hardness tester for performing materials hardness testing according to claim 1, wherein said tester further comprises means for controlling and sensing the rate of application of load to said indentor means and to the test specimens.

11. A hardness tester for performing materials hardness testing as claimed in claim 1, wherein said linear displacement transducer means is located directly above said load cell means for directly measuring displacement in the test specimen.

12. A hardness tester for performing materials hardness testing as claimed in claim 11 further comprising a specimen support platform located on a base of said tester, said specimen support platform being selectable from a plurality of specimen support platforms of differing sizes.

13. A hardness tester for performing materials hardness testing as claimed in claim 1, further comprising frame means for supporting said tester, wherein said linear displacement transducer means includes a glass scale attached to said actuator means, and a reading head attached to said frame means, wherein said glass scale moves with respect to said reading head and enables direct measurement of displacement of said actuator means.

14. A hardness tester for performing materials hardness testing as claimed in claim 13 further comprising a specimen support platform located on a base of said tester, said specimen support platform being selectable from a plurality of specimen support platforms of differing sizes.

15. A hardness tester for performing materials hardness testing as claimed in claim 1 further comprising a specimen support platform located on a base of said tester, said specimen support platform being selectable from a plurality of specimen support platforms of differing sizes.

16. A hardness tester for performing materials hardness testing as claimed in claim 1 wherein said tester comprises means for producing information about the test load and related test displacement substantially simultaneously.

17. A hardness tester for performing materials hardness testing as claimed in claim 1 wherein said tester comprises means for measuring the depth of specimen indentation from the surface of the test specimen.

18. A hardness tester for performing materials hardness testing as claimed in claim 1, wherein said motor means comprises an electric motor.

19. A hardness tester for performing materials hardness testing as claimed in claim 1, wherein said actuator means includes a ball screw.

20. A hardness tester for performing materials hardness testing as claimed in claim 1, wherein said closed loop control means further comprises a central processing unit.

* * * * *